(12) United States Patent  
Glocker (10) Patent No.: US 7,803,628 B2  
(45) Date of Patent: Sep. 28, 2010

(54) DEVICE FOR MEASURING PRESSURE

(75) Inventor: Raymond Glocker, Aschaffenburg (DE)

(73) Assignee: MHM Harzbecher Medizintechnik GmbH, Aschaffenburg (DE)

( * ) Notice: Subject to any disclaimer, the term of this patent is extended or adjusted under 35 U.S.C. 154(b) by 1004 days.

(21) Appl. No.: 10/556,141

(22) PCT Filed: Apr. 30, 2004

(86) PCT No.: PCT/EP2004/004587  
§ 371 (c)(1),  
(2), (4) Date: Aug. 23, 2006

(87) PCT Pub. No.: WO2004/098679  
PCT Pub. Date: Nov. 18, 2004

(65) Prior Publication Data  
US 2006/0275907 A1    Dec. 7, 2006

(30) Foreign Application Priority Data  
May 9, 2003 (DE) ................ 103 21 099

(51) Int. Cl.  
G01N 27/02 (2006.01)  
G01N 27/06 (2006.01)  
G01N 27/08 (2006.01)  
G01N 33/48 (2006.01)

(52) U.S. Cl. ............ 436/70; 436/63; 436/148; 436/149; 436/150; 422/73; 422/82.01; 422/82.02; 422/82.13; 73/700; 73/715; 73/725; 73/753

(58) Field of Classification Search ............ 436/70, 436/148, 149, 150, 63; 422/73, 82.01, 82.02, 422/82.13; 73/700, 715, 725, 753; 600/485, 600/561  
See application file for complete search history.

(56) References Cited

U.S. PATENT DOCUMENTS 4,572,204 A * 2/1986 Stephens .............. 600/488  
4,617,608 A 10/1986 Blonder et al. .......... 361/291

(Continued)

FOREIGN PATENT DOCUMENTS

WO    WO 01/18396 A1    3/2001

(Continued)

OTHER PUBLICATIONS

English translation of the International Preliminary Report on Patentability dated Apr. 27, 2006, in priority application No. PCT/EP2004/004587 (12 pgs).

(Continued)

Primary Examiner—Maureen M Wallenhorst  
(74) Attorney, Agent, or Firm—Grossman Tucker Perreault & Pfleger, PLLC (57) ABSTRACT

In a device for measuring the pressure of a medium, in particular a liquid medium, the device including a measuring chamber through which the medium can flow and which has at least one elastically deformable wall, at least one wall that is more rigid by comparison to the elastically deformable wall, and an inlet and outlet for the medium, at least one excitation electrode is provided in or on the at least one more rigid wall of the measuring chamber, and at least one signal electrode is provided on the elastically deformable wall, for impedance measurement.

22 Claims, 3 Drawing Sheets

U.S. PATENT DOCUMENTS

| | | | |
|---|---|---|---|
| 5,554,113 A * | 9/1996 | Novak et al. | 604/30 |
| 6,193,864 B1 | 2/2001 | Leader et al. | 204/409 |
| 6,450,972 B1 * | 9/2002 | Knoll | 600/561 |
| 6,475,750 B1 | 11/2002 | Han et al. | 435/14 |
| 6,684,710 B2 * | 2/2004 | Chevallet et al. | 73/723 |
| 2002/0151816 A1 | 10/2002 | Rich et al. | 600/547 |
| 2004/0050168 A1 * | 3/2004 | Uberreiter | 73/706 |
| 2007/0261496 A1 * | 11/2007 | Jonsson et al. | 73/723 |
| 2008/0015486 A1 * | 1/2008 | Zhang et al. | 604/4.01 |

FOREIGN PATENT DOCUMENTS

| | | |
|---|---|---|
| WO | WO 02/03854 A3 | 1/2002 |
| WO | WO 2004/024300 A1 | 3/2004 |

OTHER PUBLICATIONS

International Search Report dated Jul. 29, 2004 for corresponding application No. PCT/EP2004/004587.

Written Opinion for corresponding application No. PCT/EP2004/004587.

* cited by examiner

DEVICE FOR MEASURING PRESSURE

The invention relates to a device for measuring the pressure of a medium, in particular a liquid medium, said device comprising a measuring chamber through which the medium can flow and which has at least one elastically deformable wall, at least one wall that is more rigid by comparison to said first wall, and an inlet and outlet for the medium, and to a method for determining the hematocrit value of blood contained in a measuring chamber, in particular using the device.

Devices of this kind are used in medicine for measuring pressures in liquids in the examination and treatment of humans and animals, in particular via electronic diagnostic and monitoring appliances. To monitor the hemodynamic parameters of a patient, in particular of patients in intensive care, it is nowadays customary not simply to record an ECG, but also to include the invasive pressures in the recording, that is to say to monitor the state of the patient's vital functions. Depending on the degree of monitoring, between one and four pressures are measured, namely the arterial pressure, the pulmonary arterial pressure, the LAP, and the venous pressure.

For this purpose, a catheter with attached monitoring set is used. The positions of the openings at the end of the catheter define the measurement points in the patient's body. Monitoring set here refers to the parts which, for hygiene reasons, are intended in most cases to be disposed of after a single use and which establish the connection between the patient and the so-called monitor. Monitor designates the electronic monitoring and recording system with which the corresponding measured data can be evaluated and displayed and which, if necessary, emits corresponding alarm signals when measured data depart from predefined target ranges.

A general description of this is found in a study of a flow-directed catheter in Buchwalsky, Rainer, Flow-directed catheter: Technique, evaluation and practical consequences (Beiträge zur Kardiologie, Volume 29), Erlangen, perimed Fachbuchverlagsgesellschaft, 1985, pages 106 to 109. The monitoring set to be secured on the catheter consists in this case of an unventilated infusion appliance for delivering infusion solutions to the patients, an irrigation system which ensures a continuous irrigation rate of usually 3 ml per hour at the catheter tip in order to avoid occlusions by clots, and a pressure dome. The pressure dome transmits the pressure signal via its flexible membrane to a reusable transducer (pressure sensor). Such a pressure dome was hitherto secured on a suitable transducer by a screw connection or bayonet connection (see DE 42 19 888 A1, column 3, lines 28 to 30) or by means of snap-in hooks (cf. WO 99/37983). A further development of a pressure dome with transducer is also found in WO 02/03854. With the system disclosed in the latter publication, underpressures can be measured directly in the blood circulation which are greater than those at which red blood cells in human blood burst (hemolysis) after a relatively long action time. In addition, high pressure increase speeds can be detected.

A transducer has in particular a chip with a Wheatstone bridge. This chip can also be provided in the pressure dome as a non-reusable disposable part. In this case, a disposable transducer is then provided which measures the pressure.

Another approach is disclosed in DE 197 24 001 C1. In this case, a pressure measurement system is described which measures the variable geometric form of a column of saline solution in a catheter, by measuring the electrical resistance, the electrical capacitance or acoustic cavity resonance, in order to determine the pressure profile which causes the geometric change via at least one catheter wall acting on the column of saline solution. Here, therefore, the compression of the catheter wall is determined, the tube being filled continuously from one end with a liquid substance which displaces the substance located in the tube, in most cases a gas, until a defined filling length $x_A$. This filling length $x_A$ is determined. The pressure profile measurement is carried out on the basis of a capacitance measurement, the tube being made of an electrically insulating material, and the capacitance being measured with the aid of a capacitance meter between the electrically conductive filling and an electrically conductive medium arranged outside the tube, said electrically conductive medium completely surrounding the tube.

Since the provision of air or of another gas is not feasible or practical in particular when measuring pressures in the blood of a human or animal, the device disclosed in DE 197 24 001 C1 cannot be used for pressure measurements particularly in the field of dialysis.

The object of the present invention, therefore, is to develop a device for measuring the pressure of a medium, in particular a liquid medium, in such a way that pressure measurement is also possible without the provision of a costly transducer, and that this device can also be used in particular for dialysis and other mechanical applications in which pressures are to be measured.

The object is achieved, by the fact that at least one excitation electrode is provided in or on the at least one more rigid wall of the measuring chamber, and at least one signal electrode is provided on the elastically deformable wall, for impedance measurement. The object is also achieved, for a method for determining the hematocrit value of blood contained in a measuring chamber, by the fact that blood flows through the measuring chamber in an extracorporeal circuit, and the hematocrit value is determined by determining the conductivity value between two fixed electrodes projecting into the measuring chamber. Developments of the inventions are defined in the dependent claims.

In this way, a device for measuring the pressure in a medium is made available which can be produced relatively inexpensively and can also be used as a disposable article. Just the one device is provided as a unit, which, in contrast to the pressure domes with transducer according to the prior art, is therefore more compact and easier to handle. Since no laborious joining of transducer and pressure dome is necessary, the measurement itself is also more reliable, because inaccuracies resulting from incorrect connection of transducer and pressure dome do not arise. Correct use thus no longer depends on the correct assembly of transducer and pressure dome. In contrast to the sensor device disclosed in DE 197 24 001 C1 and used for measuring pressure, the device according to the present invention can also be used especially effectively for measuring pressure in dialysis, since the presence of gas or air inside the measuring chamber is not necessary, and it is instead a liquid medium in particular that flows through the measuring chamber. The device according to the invention can also be used as a replacement for existing transducer and pressure dome systems, since it can easily be adapted to the retaining means of the pressure dome and transducer combinations known in the prior art. It is therefore not even necessary to change existing retaining means for the pressure measurement devices. Additional costs involved in doing this are therefore avoided.

An excitation system is preferably provided for supplying the at least one excitation electrode arranged in or on the measuring chamber. The excitation system particularly preferably delivers a high-frequency alternating current of low current intensity, and, in particular, the alternating current is adjustable. To avoid electrolysis and to ensure a patient's safety (IEC 601-1), so as to protect him from electric shock, a high-frequency alternating current of low current intensity is advantageously used. In this connection, the at least one excitation electrode is preferably made of a material providing good conduction of high-frequency alternating currents, and, in particular, is hard silver-plated. Any other desired material having good conductivity for high-frequency alternating currents can also be used.

The elastic wall is preferably made of a reversibly deformable material, in particular an elastomer. This reliably ensures a deflection of the elastic wall at all times, but also, when the pressure changes, a recovery movement of the elastic wall too. The at least one signal electrode is preferably designed substantially flat, in particular as a film material, conductive coating, conductive imprint and/or lacquer. The signal electrode is particularly preferably applied onto the elastic wall of the measuring chamber by a vacuum deposition method or is sprayed on, adhesively bonded on or otherwise applied. This ensures that the signal electrode is as thin as possible and that, therefore, the elasticity or reversible deformability of the elastic wall is not limited. This is intended largely to rule out any distortion of the results.

The measuring chamber is preferably provided with attachments for connection of a catheter, in particular in the area of the inlet and outlet for the medium. A Luer lock, tube attachments, etc., can be provided for this connection. Instead of just one elastically deformable wall, it is also possible to provide several of these elastically deformable walls. As the medium to be measured flows through the measuring chamber, the latter is subjected to a pressure which represents the differential pressure in relation to the atmospheric pressure outside the measuring chamber. The elastic wall is accordingly deformed by this pressure difference. Between the excitation electrode in the more rigid wall part of the measuring chamber and the signal electrode in the elastic wall part, a change of impedance is determined on the basis of the change of volume of the measuring chamber, said change of impedance affecting the medium that fills the measuring chamber, which medium is in particular an electrically conductive liquid. In the case of an invasive pressure measurement, the measuring chamber is flushed with a physiological saline solution at a concentration of in particular 0.8% by volume. In the case where the device is used in extracorporeal circuits, whole blood is conveyed through the measuring chamber.

Preferably, the at least one elastic wall is or can be connected to the other walls of the measuring chamber by a tongue-and-groove joint. In particular, the elastic wall has an annular bead element on its edge facing toward the other walls, and the walls which are or can be connected to the elastic wall have at least one groove for insertion of the bead element. The work involved in assembling the device is reduced by this means, since the annular surrounding bead element engages into the groove on the other, more rigid walls. A tight and at the same time self-adjusting connection is thus automatically established. This connection can even be subsequently undone and can then be firmly made again without any problems.

An arrangement is preferably provided for ensuring free mobility of the elastic wall. The arrangement is particularly preferably a protective cap, or a recess which permits free mobility of the elastic wall and which is situated in a retaining means for securing the device in the area of the measuring chamber. In particular, the protective cap and/or the recess in the retaining means has such a shape and such dimensions, and is arranged in the area of the elastic wall such that it forms an abutment surface for the latter for pressure limitation. To permit in principle a free mobility of the elastic wall, the protective cap is fitted. The base part of the latter then surrounds the elastic wall of the measuring chamber. Alternatively (or in addition), the retaining means on which the device, and in particular the measuring chamber, is fitted can also assume the function of the protective cap. It is for this purpose that the retaining means comprises the recess, so that a space is again created within which the elastic wall is able to move. The elastic wall is in particular a membrane.

When measurements are being carried out on a patient's blood, the measuring chamber on the retaining means can be arranged in such a way as to set a correct measurement position at the level of the right atrium of the heart, in order to generate a correct zero-point determination. In order to provide an abutment, despite the creation of a space for movement of the elastic wall, the protective cap, or the recess in the retaining means, in particular the retaining plate thereof, is preferably configured in such a way that the elastic wall abuts against the protective cap, or abuts against the recess in the retaining means, at circa 800 mmHg. When such an abutment is provided, the approach of the pressure limit can be indicated by sensors visually and/or acoustically or in some other way. When the pressure limit is reached, an emergency signal can be output. An arrangement is preferably provided for adjusting the device and for holding it at an adjustable height, this arrangement in particular being provided on the retaining means. In this way, it is possible in particular to fit the measuring chamber into the retaining means such that it performs a measurement at the level of the atrium. In addition, the measuring chamber can have in at least some areas a means for coupling out capacitive fields and/or can be surrounded by a means acting as a Faraday cage, and in particular the measuring chamber and/or the retaining means is/are provided with a metallic coating. In this way, it is advantageously possible to ensure that capacitive fields which act from outside on the measuring chamber, and which could otherwise distort the impedance measurement in the measuring chamber, can be screened off in the manner of a Faraday cage. It is also possible, for example, to electroplate or coat the retaining means for the measuring chamber so as to form such a Faraday cage to keep capacitive interference fields out of the measuring chamber. In particular, the receiving part for the measuring chamber on the retaining means can, for this purpose, be designed as an open hollow profile.

In a device for measuring the pressure of a medium, in particular a liquid medium, said device comprising a measuring chamber through which the medium can flow and which has at least one elastically deformable wall, at least one wall that is more rigid by comparison to said first wall, and an inlet and outlet for the medium, it is advantageous, in order to determine the conductivity of a medium located in the measuring chamber, to provide an excitation electrode and a second electrode outside the elastic wall. By provision of this combination of excitation electrode and second electrode, neither of which is provided in the elastic wall, but instead in the more rigid walls, it is possible to determine the conductivity within the medium located in the measuring chamber. In this case, the second electrode is likewise in particular in contact with the interior of the measuring chamber.

When blood flows through the measuring chamber, the hematocrit value can be determined from the conductivity value of the blood. A calculation of the hematocrit value is also possible, for example, with automated blood gas analyzers. The hematocrit value represents the proportion of solids relative to serum in the blood. From the hematocrit value, or the proportion of solids relative to serum, it is possible to determine the intake and output of liquids, that is to say to determine a liquid balance, and it is also possible to determine whether addition of liquid, in particular of saline solution, by infusion is necessary. Specifically in dialysis, a loss of liquid may take place during preparation of the blood. In conventional methods, the blood is continuously weighed in order to determine the hematocrit value. However, since the balances used for this are very expensive, it proves advantageous, in the present method, to determine the hematocrit value from determination of the conductivity value. Preferably, a pump is provided in the area where blood is removed, and a further pump is provided in the area where the blood is returned to the patient's body. A sensor is likewise arranged upstream and downstream of each pump. In this case, it is particularly preferred to configure the first and last sensor, that is to say the sensor upstream of the first pump and downstream of the last pump, as a conventional pressure dome, with a transducer, and to configure the two middle sensors in the form of the device for measuring pressure according to the present invention. In this way, a liquid balance can be established easily and quickly, since the devices according to the present invention are able to provide results very rapidly, the hematocrit values at the blood collection and at the blood return being compared with one another.

An evaluation unit is preferably provided for determining the hematocrit value from the determined conductivity value and/or the internal pressure of the measuring chamber and in particular for correction of its zero line and sensitivity. From the conductivity measurement, it is possible, in particular by a computer-aided evaluation method, to calculate the hematocrit value (by determining the measured values of the two electrodes arranged in the more rigid walls) and the internal pressure of the measuring chamber (by determining the impedance between the one electrode arranged in the more rigid wall and the other electrode arranged in the elastic wall). By comparing the conductivity value and the internal pressure value, it is additionally advantageously possible to obtain a correction of the zero line and sensitivity, since the measured impedances depend on the dielectric properties of the medium in the measuring chamber, which dielectric properties, when the device is used in extracorporeal circuits, may vary on account of the change in the hematocrit value of the blood flowing through the measuring chamber. The determination of the conductivity value is based on the rule that the conductivity is the inverse value of the specific resistance. This specific resistance can be determined between the two electrodes arranged in the more rigid walls of the measuring chamber. Since the impedance measurement takes place as a function of the frequency, a determination of the conductivity between the one fixed electrode and the other electrode arranged in the elastic wall does not prove particularly expedient, since disturbance variables arise here.

At least one contact pin is preferably provided for attaching the measuring chamber onto the retaining means. The retaining means preferably has a retaining plate which is provided with contact surfaces or contact pads and which is used to generate concealed contacting between retaining means and measuring chamber. The contact surfaces and/or contact pads and the contact pins are preferably distributed in such a way that false contacting and false polarity are substantially avoided. The provision of contact pins makes it easier to connect the electrodes to corresponding connection arrangements in the area of the retaining means. To avoid laborious insertion of one into the other, contact surfaces or contact pads are in particular provided there. In this way, the contact pins and contact surfaces preferably just rest on one another. However, openings can also be provided in the retaining means, in particular the retaining plates thereof, into which openings the contact pins can be inserted. This also results in contacting that is covered from the outside. Each of the electrodes can be provided with one contact pin, and a corresponding number of contact pads or contact surfaces, in particular openings for insertion of the contact pins, are advantageously provided on the retaining means or retaining plate.

To avoid false polarity or false contacting of the electrodes and contact surfaces or contact pads, a specific geometrical arrangement of the contact pins and contact surfaces is in particular chosen such that these only fit one another in a specific orientation. When connecting the measuring chamber to the retaining means, care must be taken to ensure that the correct electrodes are excited and that the signals are taken likewise from the signal electrodes or the signal electrode on the elastic wall. As an alternative to the suitable geometric arrangement, other measures can also be taken to ensure correct positioning and to avoid false polarity and incorrect contact. For example, the respective shapes of the contact pins and contact surfaces or contact pads can also be adapted to one another.

At least some of the contact pins and electrodes are preferably formed integrally. Particularly preferably, the contact pins and electrodes are molded onto the measuring chamber, in particular in an insert injection-molding operation. The provision of integrally formed contact pins and electrodes reduces the amount of material used, since just one part has to be provided, and connection of two parts is not needed. Assembly is also made easier given that two elements do not have to be connected to one another. Assembly and production is made particularly easy if contact pins and electrodes are already molded onto the measuring chamber, in particular in the insert injection-molding operation, since, with the provision of a suitable shape, the contact pin/electrode combination simply has to be inserted into the mold at suitable locations, after which the measuring chamber is molded on top. The reproduction and unambiguous positioning of the contact pins and electrodes, especially also in respect of their continuation into the interior of the measuring chamber, is in this case particularly simple and precise.

The protective cap preferably has a base part for protecting the elastic wall of the measuring chamber, and a collar part which at least partially surrounds the area of the electrodes and/or contact pins so as to protect the contact pins. In this way, not only is the elastic wall or membrane protected, but also the contact pins, in particular the integrally formed contact pins, even inside the rigid walls of the measuring chamber. In this case, the collar part can extend so far along the height of the measuring chamber that the contact pins are safely protected. Instead of a surrounding collar part, it is in particular also possible to provide only a partially surrounding collar part for protecting the contact pins. In this case, however, care must be taken to ensure the correct positioning of the protective cap, especially in the area of the collar part, so as to reliably protect the contact pins.

The invention is explained in more detail below on the basis of illustrative embodiments and with reference to the drawings, in which.

Figure 1:
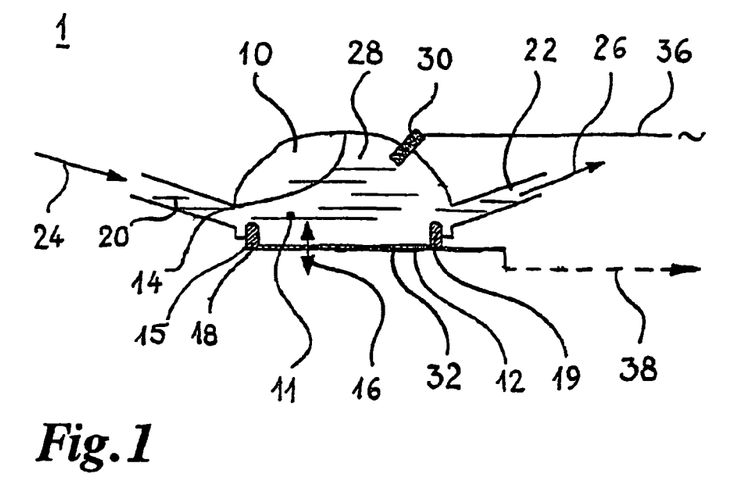
FIG. 1 shows a cross-sectional side view of a first embodiment of a device for measuring pressure according to the invention.

FIG. 1 is a schematic representation of a first embodiment of a device 1 according to the invention for measuring pressure, shown here in cross section and from the side. The device has a measuring chamber 10 with an elastic wall 12 and a substantially rigid wall 14. A double arrow 16 indicates the elastic mobility of the elastic wall 12. The measuring chamber has an inlet 20 for medium and an outlet 22 for medium. A medium 28 is present inside the measuring chamber. This medium 28 is indicated simply by short lines. Arrows 24 and 26 indicate the inflow (24) and outflow (26) of the medium.

The connection between the elastic wall 12 and the substantially rigid wall 14, which is dome-shaped, is formed via a bead element 18. This bead element 18 is applied in a surrounding manner on the elastic wall 12 in the area of an outer edge 15, in particular being integrally connected thereto. The bead element engages in a circular groove 19 in the substantially rigid wall 14. In this way, a connection is achieved which is substantially secure against escape of liquid.

For measuring pressure, a first electrode 30 is arranged in the substantially rigid wall 14. Part of this first electrode 30 protrudes through the wall 14 and into the interior 11 of the measuring chamber. A second electrode 32 is arranged on the outer face of the elastic wall 12. This second electrode 32 is very flat and is not in direct electrical contact with the interior 11 of the measuring chamber. The first electrode is connected, via an excitation current supply line 36, to an excitation current source for alternating current (not shown in FIG. 1). The second electrode 32 takes the signals it has detected and transmits them, for example, to an evaluation unit (not shown in FIG. 1) via a signal line 38. A medium 28, for example a saline solution in the case of invasive pressure measurement, or whole blood in the case of extracorporeal pressure measurement, can flow through the interior of the measuring chamber 10. In the traditional medical technique for invasive measurement of pressure, it is customary to apply 300 mmHg of pressure to a catheter by means of a bag of saline solution with cuff and to limit a flow reducer (of an irrigation system) to a flow of 3 mm per hour and to allow a flow of physiological saline solution of 0.8% by volume in order to prevent occlusion of the catheter tip by a clot. This saline solution flowing in any case through the catheter can here be used for measuring pressure. When it has liquid flowing through it, its variable volume within the measuring chamber moves the flexible membrane or elastic wall 12. The saline solution also flows past the electrode 30, by which means a mechanical-electrical pressure transducer can determine the change in impedance by comparing the pressure difference between the first and second electrodes and thus also the change in resistance in this area.

In an extracorporeal circuit, blood can flow through the measuring chamber, in which case, depending on the composition of the blood, the different dielectric properties can lead to different basic signals (baseline). In the blood composition, the proportion of solids, corresponding to hematocrit, relative to the liquid proportion, corresponding to serum, can vary from patient to patient and from measurement to measurement. However, the relative pressure differences in the area of the measuring chamber can be determined at the correct proportions independently of the blood composition in each case.

Figure 3:
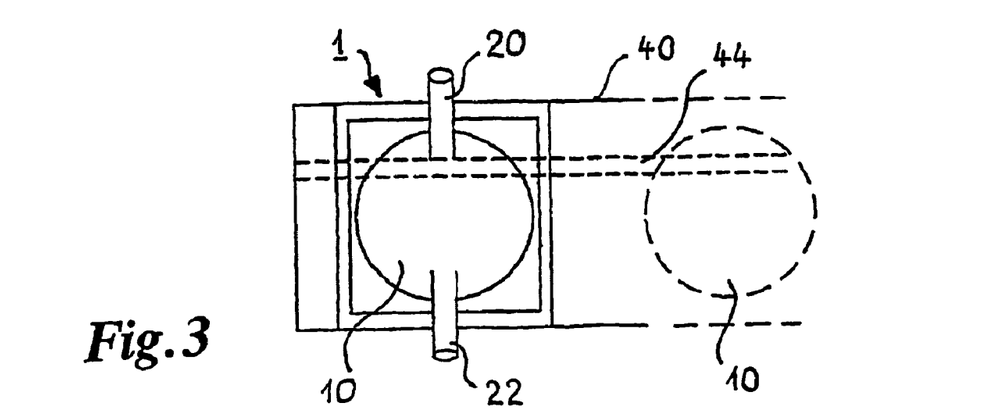
FIG. 3 shows a plan view of a further embodiment of a device for measuring pressure according to the invention, with a retaining means in the form of a hollow profile.

The device 1, in particular the measuring chamber 10, can be fitted in a conventional manner into a retaining means 40 which, for example, is secured on an infusion stand. Such a retaining means 40 is shown schematically in FIGS. 3 and 4. As can be seen particularly clearly from FIG. 4, this retaining means can be in the form of an open hollow profile which has a recess 42 in the area of the elastic wall 12 of the measuring chamber 10. By this means, a free mobility of the elastic wall is possible, as is again indicated by the double arrow in FIG. 4. FIG. 3 shows that several such devices for measuring pressure can be arranged alongside one another in such a retaining means 40, in which case the retaining means has, on its underside, a rail 44 which can be secured, for example, on an infusion stand, in particular by being clamped or being pushed into a corresponding receiver.

Figure 4:
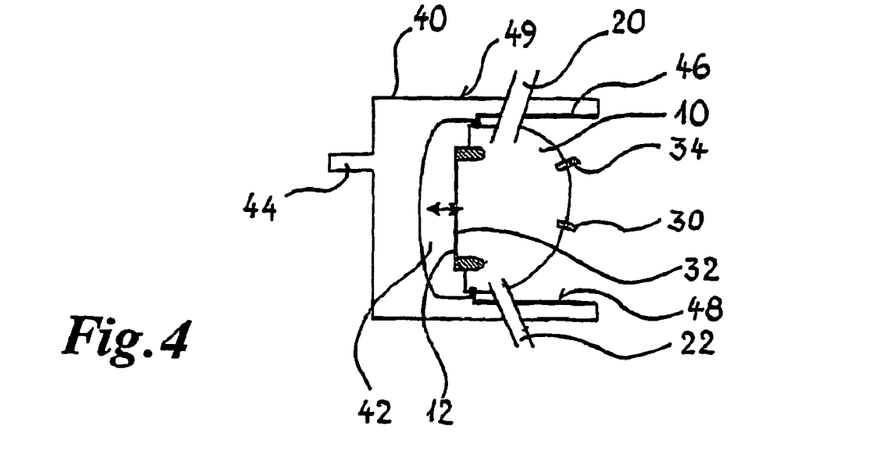
FIG. 4 shows an end view of the device of FIG. 3.

The retaining means can be made of plastic, but it preferably has a metallic coating 46 in order to form a Faraday cage about the measuring chamber. In this way, capacitive interference from outside is screened off. Such capacitive interference could distort the measurement of impedance in the area of the measuring chamber. The coating 46 can be provided on the inner face 48 or on the outer face 49 of the retaining means. It can also be provided on both sides.

Figure 2:
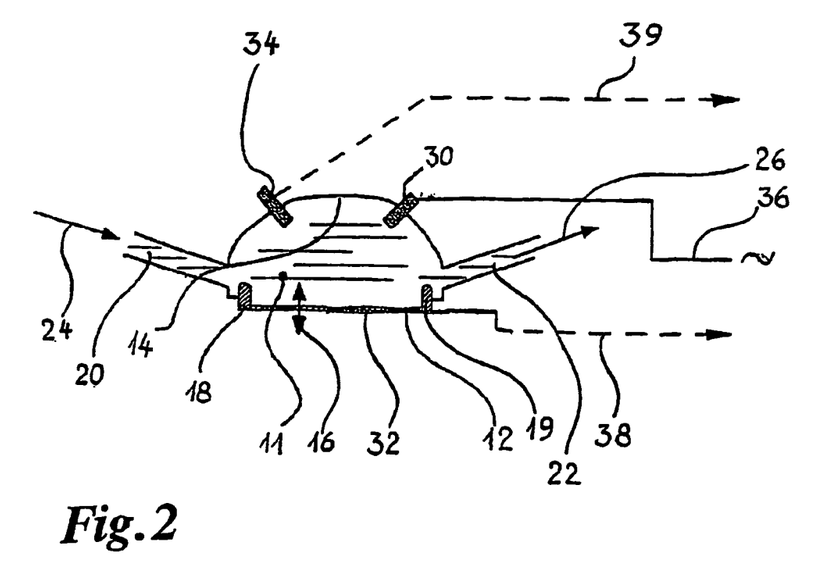
FIG. 2 shows a cross-sectional side view of a second embodiment of a device for measuring pressure according to the invention.

As can be seen in particular from FIG. 2, a further, third electrode 34 can be arranged in the rigid wall 14 in addition to the first electrode 30 provided in said substantially rigid wall 14. This third electrode 34 likewise preferably protrudes into the interior 11 of the measuring chamber and also outward through the wall, in the same way as the first electrode 30. The third electrode 34 is provided for measuring the conductivity of the medium flowing through the measuring chamber. Like the first electrode 30, the third electrode 34 is in contact too with the interior 11 of the measuring chamber. In particular when blood flows through the measuring chamber, the hematocrit value can be determined from the conductivity measurement. The conductivity measurement takes place between the first electrode and the third electrode. The first electrode is once again the excitation electrode, and the third electrode delivers the signal. The first electrode 30 is therefore connected to an alternating current/excitation current source via the excitation current supply line 36, and the third electrode 34 delivers signals via a signal line 39, for example to an evaluation unit. To be able to convert the proportional pressure values into absolute pressure values, it is possible, by determining the hematocrit value in a computer-aided evaluation operation, to make a necessary correction to obtain the correct basic signal, in which case, as has already been mentioned above, different basic signals or baselines may be present on account of different blood compositions and, consequently, different dielectric properties of the blood present in the measuring chamber. The proportional pressure values can thus be converted into absolute pressure values and can thus also be compared to other pressure values.

Figure 5A:
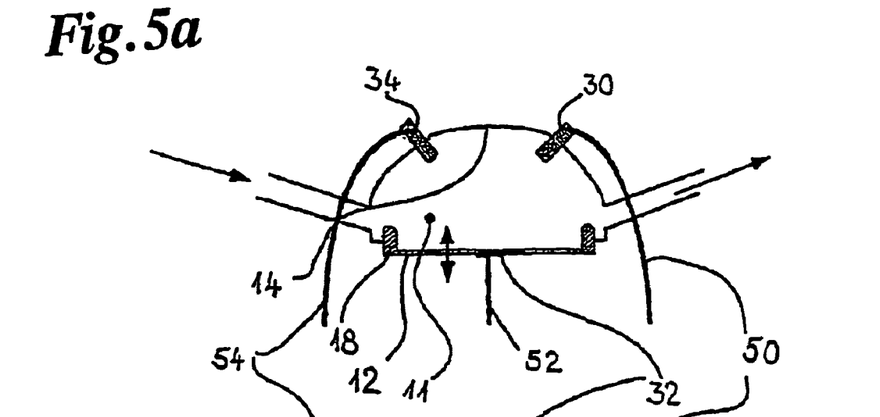
FIGS. 5a) and 5b) show a cross-sectional side view and a plan view, respectively, of a modified embodiment of the embodiment according to FIG. 2, in which contact pins are provided, and FIGS. 6a) and 6b) show a cross-sectional side view of the embodiment of the device for measuring pressure according to FIG. 5, fitted into a protective cap.
Figure 5B:
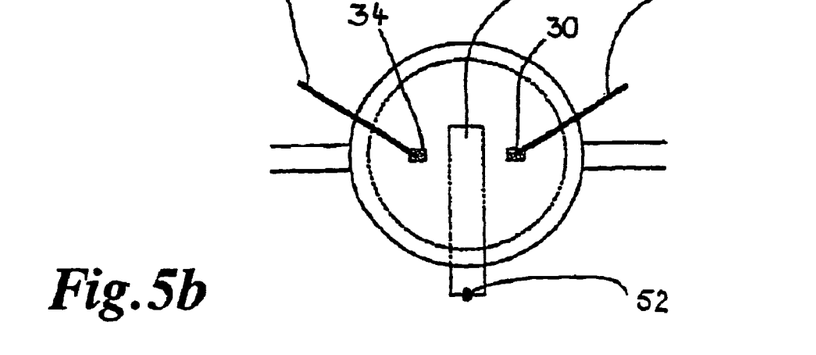

In order to input the necessary excitation voltage or excitation current to the device 1, in particular a voltage of 2 volts and an alternating current of 100 kHz, from an excitation circuit in a defined and secured form, in particular in compliance with IEC 601-1-1, and in order to collect the signal or signals (conductivity value and pressure) emitted by the device at the electrode 32 and transfer this to an evaluation unit, the retaining means is provided with contact surfaces or contact sites for connection to the electrodes of the measuring chamber. This permits input and output of the high-frequency alternating current. Since, as regards use in hospitals, relatively little or no attention is paid to clean contact surfaces, it is advantageous for these contact surfaces or contact sites in the area of the retaining means to be covered as far as possible. This also safely and in a problem-free manner permits frequent contacting between the retaining means, in particular suitable retaining plates provided thereon, and the measuring chamber or device 1, which in particular is a single-use or disposable article, without the problem of contact interferences. As can be seen in particular from FIGS. 5a and 5b, the electrodes 30, 32 and 34 are provided with contact pins 50, 52 and 54. The contact pins can be produced separately and connected to the electrodes, or they can be formed integrally with these. An integral configuration is not only simpler in production terms, it also does not entail the risk of the contact pins coming loose from the electrodes on account of defective soldered connections or the like. The contact pins in principle constitute an extension of the respective electrodes, so as to be able to attach the electrodes to the corresponding contact surfaces, which are not shown in FIG. 5, but are provided inside the retaining means. As can be seen from the plan view in FIG. 5b, the signal electrode or second electrode 32 is extended so far that the contact pin 52 lies outside the actual measuring chamber and, consequently, is more easily connected to the retaining means. In the embodiment shown in FIG. 5a, all the contact pins are drawn downward. However, other configurations may also be chosen. Preferably, the length and shape and the arrangement of the contact pins are also adapted to the respective retaining means.

Figure 6A:
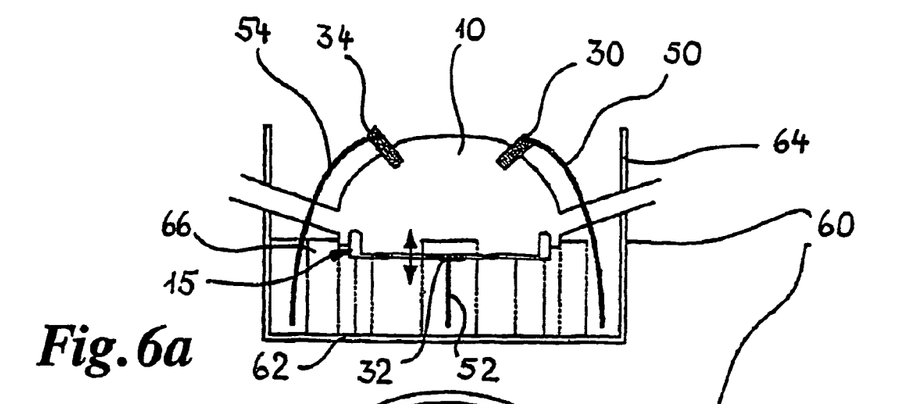
Figure 6B:
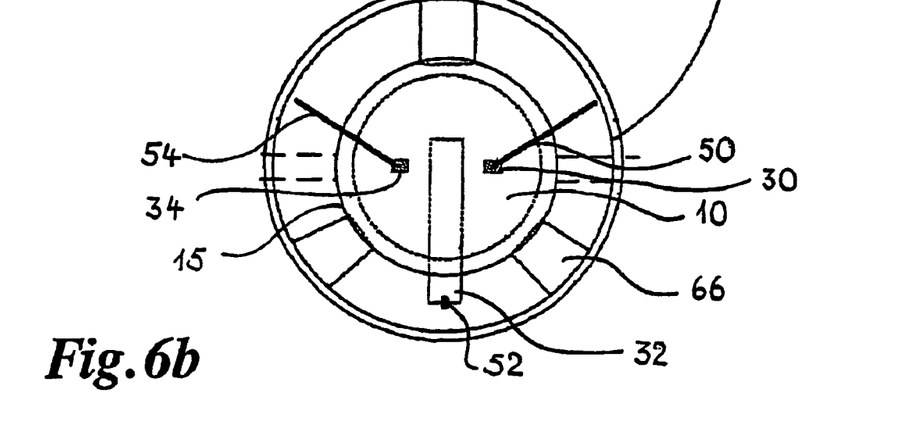

In order to protect the contact pins, a protective cap 60 can be provided. This is shown in FIGS. 6a and 6b. The protective cap shown in FIGS. 6a and 6b has a base part 62 and a surrounding collar part 64. This surrounding collar part is extended to such a height that both electrodes 30, 34 arranged on the top of the measuring chamber are protected against external damage. In order to leave a sufficient space between the base part and the elastic wall of the measuring chamber, the protective cap has spacers 66 which are arranged on the base part and bear on the outer edge 15 of the substantially rigid wall 14 of the measuring chamber. This can be seen in particular in the plan view in FIG. 6b. The protective cap not only protects the contact pins against external action, it also protects the other component parts of a tube set, to which the measuring chamber and device for measuring pressure belong or to which they can be connected, from damage caused by the contact pins, in particular by scratching of the tube wall and consequently from damage to the latter.

The devices for measuring pressure which are shown in the figures are all round in cross section. However, they can also have any other desired shape, in particular polygonal. The protective cap, too, can have a shape different than the measuring chamber if such proves advantageous, in particular for application on a retaining means.

To establish a liquid balance, the devices for measuring pressure which are shown in the preceding figures and which have been described can also be combined with conventional pressure domes with transducers. In this case, for example, a pairing can be provided consisting of a conventional pressure dome with transducer upstream of a pump and a device according to the invention for measuring pressure downstream of this pump. The liquid balance is then obtained by comparison of the conductivity values or hematocrit values at the start of the measurement path and at the end of the measurement path. This measurement path can, for example, be the path through a dialysis apparatus.

In addition to the embodiments described above and shown in the figures, many others are also possible in which a pressure measurement is provided by combination of an electrode in a more rigid wall of a measuring chamber and an electrode on an elastic wall of the measuring chamber or a membrane for pressure measurement. For measurement of conductivity, two electrodes arranged in particular in a more rigid wall of a measuring chamber can be used, in which case one of these electrodes preferably serves as excitation electrode and the other as signal electrode. In the pressure measurement, the electrodes arranged on the elastic wall or membrane are preferably used as signal electrodes, and the electrodes arranged in the more rigid wall as excitation electrode. The shape and size of the respective measuring chambers can be chosen as specifically desired and as a function of the medium that is to be measured, in particular a liquid.

LIST OF REFERENCE NUMBERS

1 device for measuring pressure
10 measuring chamber
11 interior
12 elastic wall
14 substantially rigid wall
15 outer edge
16 double arrow
18 bead element
19 groove
20 inlet for medium
22 outlet for medium
24 arrow
26 arrow
28 medium
30 first electrode
32 second electrode
34 third electrode
36 excitation current supply line
38 signal line
39 signal line
40 retaining means
42 recess
44 rail
46 coating
48 inner face
49 outer face
50 contact pin
52 contact pin
54 contact pin
60 protective cap
62 base part
64 surrounding collar part
66 spacer

The invention claimed is:

1. Device for measuring the pressure of a liquid medium, said device comprising a measuring chamber through which the medium can flow and which has at least one elastically deformable wall, at least one wall that is more rigid by comparison to said deformable wall, and an inlet and outlet for the medium, wherein at least one excitation electrode is provided in or on the at least one more rigid wall of the measuring chamber, and at least one signal electrode is provided on the elastically deformable wall wherein a measure of impedance between the electrodes as a liquid medium flows through the measuring chamber serves to measure the pressure of the liquid medium.

2. Device according to claim 1, wherein an excitation system is provided for supplying alternating current to the at least one excitation electrode.

3. Device according to claim 2, wherein the excitation system delivers a relatively high-frequency alternating current of relatively low current intensity, and, the alternating current is adjustable.

4. Device according to claim 1, wherein the at least one excitation electrode is made of a material providing good conduction of relatively high-frequency alternating currents, and, is hard silver-plated.

5. Device (1) according to claim 1, wherein the at least one elastically deformable wall is made of a reversibly deformable elastomeric material.

6. Device according to claim 1, wherein the at least one signal electrode is designed substantially flat, being applied as a film material, conductive coating, conductive imprint and/or lacquer, onto the at least one elastically deformable wall of the measuring chamber by a vacuum deposition method or being sprayed on, or adhesively bonded on.

7. Device according to claim 1, wherein the at least one elastically deformable wall is or can be connected to the other walls of the measuring chamber by a tongue-and-groove joint, the at least one elastically deformable wall having an annular bead element on its edge facing toward the other walls, and the walls which are or can be connected to the at least one elastically deformable wall having at least one groove for insertion of the bead element.

8. Device according to claim 1, wherein said at least one elastically deformable wall has freedom to move in or out with respect to said chamber.

9. Device according to claim 8, wherein a protective cap, or a recess is situated in a retaining means for securing the device, the cap or recess providing said freedom for said at least one elastically deformable wall to move in or out.

10. Device according to claim 9, wherein the protective cap and/or the recess in the retaining means is arranged in the area of the at least one elastically deformable wall such that the at least elastically deformable wall abuts said cap or recess.

11. Device according to claim 9, wherein said device may be adjusted and held at an adjustable height on the retaining means.

12. Device according to claim 9, wherein the measuring chamber has in at least some areas a means for coupling out capacitive fields and/or is surrounded by a means acting as a Faraday cage, and the measuring chamber and/or the retaining means is/are provided with a metallic coating.

13. Device according to claim 9, wherein in order to determine conductivity of the medium located in the measuring chamber, said at least one excitation electrode and a second electrode are provided outside the at least one elastically deformable wall.

14. Device according to claim 13, said device including a retaining means, wherein at least one contact pin is provided for attaching the measuring chamber onto the retaining means.

15. Device according to claim 14, wherein the retaining means has a retaining plate which is provided with contact surfaces or contact pads to provide contact between the retaining means and the measuring chamber.

16. Device according to claim 15, wherein the contact surfaces and/or contact pads and the contact pins are distributed in such a way that false contacting and false polarity are substantially avoided.

17. Device according to claim 14, wherein at least some of the contact pins and said excitation and said second electrodes are formed integrally.

18. Device according to claim 17, wherein the contact pins and the excitation and said second electrodes are molded onto the measuring chamber, in an insert injection-molding operation.

19. Device according to claim 14, wherein the protective cap has a base part for protecting the at least one elastically deformable wall of the measuring chamber, and a collar part which at least partially surrounds the area of the excitation and said second electrodes and/or contact pins so as to protect the contact pins.

20. Method for determining the a hematocrit value of blood contained in a measuring chamber, using the device of claim 13, comprising:
providing a measuring chamber through which the blood can flow and which has at least one elastically deformable wall, at least one wall that is more rigid by comparison to said at least one elastically deformable wall, and an inlet and outlet for the blood,
providing at least one excitation electrode and a second electrode in or on the at least one more rigid wall of the measuring chamber, said at least one excitation electrode and said second electrode projecting into said measuring chamber,
allowing the blood to flow through the measuring chamber in an extracorporeal circuit, and
determining the hematocrit value of the blood by measuring a conductivity value between the at least one excitation electrode and the second electrode.

21. Method according to claim 20, wherein, the hematocrit value is determined by calculating a conductivity value at the start of a measurement path located at the inlet of the measuring chamber and at the end of the measurement path located at the outlet of the measuring chamber, and comparing the conductivity values at the start and the end of the measurement path.

22. Device according to claim 1, wherein said device measures conductivity between the electrodes as a liquid medium flows through the measuring chamber which serves to measure a hematocrit value, wherein an evaluation unit is provided for determining the hematocrit value from the determined conductivity and/or the internal pressure of the measuring chamber.

* * * * *

UNITED STATES PATENT AND TRADEMARK OFFICE
CERTIFICATE OF CORRECTION

Page 1 of 1

PATENT NO. : 7,803,628 B2
APPLICATION NO. : 10/556141
DATED : September 28, 2010
INVENTOR(S) : Raymond Glocker It is certified that error appears in the above-identified patent and that said Letters Patent is hereby corrected as shown below:

In column 11, line 9, in claim 5, after "Device" delete "(1)".

In column 11, line 37, in claim 10, delete "least" and insert -- least one --, therefor.

In column 12, line 22, in claim 20, before "a" delete "the".

Signed and Sealed this
Eleventh Day of January, 2011

David J. Kappos
*Director of the United States Patent and Trademark Office*